(12) United States Patent
Buechner (10) Patent No.: US 8,256,308 B2
(45) Date of Patent: Sep. 4, 2012

(54) METHOD AND DEVICE FOR PROVIDING BLOOD CONSTITUENTS

(75) Inventor: Karl-Heinz Buechner, Ottersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/206,830

(22) Filed: Aug. 10, 2011

(65) Prior Publication Data

US 2012/0000299 A1    Jan. 5, 2012

Related U.S. Application Data

(63) Continuation of application No. PCT/EP2010/000908, filed on Feb. 15, 2010.

(30) Foreign Application Priority Data

Feb. 17, 2009 (EP) .................................. 09152982

(51) Int. Cl.
     *B01L 3/02* (2006.01)
(52) U.S. Cl. ..................................... 73/864.02; 422/507
(58) Field of Classification Search ........................ None
See application file for complete search history.

(56) References Cited

U.S. PATENT DOCUMENTS

| | | | |
|---|---|---|---|
| 3,475,127 A | 10/1969 | Gilford | |
| 3,779,083 A | 12/1973 | Ayres et al. | |
| 3,926,521 A * | 12/1975 | Ginzel | ............................ 356/39 |
| 3,938,392 A * | 2/1976 | Rodrigues | ................... 73/864.11 |
| 3,952,599 A * | 4/1976 | Ayres | .......................... 73/864.02 |
| 4,066,407 A | 1/1978 | Lupica | |
| 4,963,498 A * | 10/1990 | Hillman et al. | .................. 436/69 |
| 5,257,984 A * | 11/1993 | Kelley | ............................. 604/403 |
| 5,456,885 A | 10/1995 | Coleman et al. | |
| 6,793,885 B1 * | 9/2004 | Yokoi et al. | .................... 422/401 |

FOREIGN PATENT DOCUMENTS

| | | |
|---|---|---|
| DE | 2724465 A1 | 12/1978 |
| DE | 29520918 U1 | 6/1998 |
| DE | 10106362 B4 | 3/2005 |
| WO | 9002516 A1 | 3/1990 |

OTHER PUBLICATIONS

International Search Report from WO 2010/094440A1, mailed Apr. 22, 2010.

* cited by examiner

*Primary Examiner* — Robert R Raevis
(74) *Attorney, Agent, or Firm* — Roche Diagnostics Operations, Inc.

(57) ABSTRACT

A metering capillary and method for providing at least one defined volume of a target constituent of a sample is provided, the method comprising providing at least one metering capillary having at least two openings; at least partly filling the metering capillary with the sample; carrying out a constituent separation for the at least partial separation of at least two constituents of the sample inside the metering capillary; and dividing the metering capillary into at least two partial pieces, wherein at least one of the partial pieces contains the defined volume of the target constituent.

20 Claims, 4 Drawing Sheets

METHOD AND DEVICE FOR PROVIDING BLOOD CONSTITUENTS

BACKGROUND OF THE INVENTION

The invention relates to a method for providing at least one defined volume of a target constituent of a sample, in particular of a blood sample. The invention further relates to a metering capillary and a device for providing at least one defined volume of a target constituent of a sample. Such methods, metering capillaries and devices can be used in particular to obtain defined amounts of plasma from capillary blood.

Testing samples of body fluids, for example blood, is often an important part of medical diagnosis. Such testing can be carried out in hospitals and also in the point-of-care sector or in home monitoring. The invention described below is concerned particularly with blood samples, although other types of samples, in particular liquid samples and preferably body fluids, can also be tested analogously. Without limitation in respect of other possible types of samples, the invention is described below mainly with reference to blood samples.

The samples are generally provided for at least a medical and/or diagnostic use. In a diagnostic use, they can be tested, for example, in respect of at least one property, for example at least one parameter that can be measured physically and/or chemically or biochemically. For example, the samples can be subject to a qualitative and/or quantitative detection of at least one analyte, in particular of at least one metabolite. For this purpose, numerous detection methods are known from the prior art.

For example, it is possible to detect glucose, cholesterol, triglycerides, hemoglobin, urea, alanine aminotransferase (ALT), aspartate aminotransferase (AST), gamma-glutamyl transferase (GGT), creatinine (CREA) or high-density lipoprotein cholesterol (HDLC), or combinations of the analytes mentioned or of other analytes. In addition, other properties of the blood can be determined, for example a proportion of corpuscular constituents (hematocrit value).

A problem of testing blood samples for example, but also other types of samples, is that these blood samples in many cases have to be worked up prior to further use. In particular, it is necessary for many uses to break blood samples down into their constituents and, for example, to separate blood plasma from corpuscular constituents of the blood sample. This separation of the blood sample into its constituents generally has to be carried out very carefully, since many measurements require a high level of purity, i.e., a high degree of separation, at the same time with exactly defined quantities of sample. In many cases, these strict requirements in terms of the precision of the sample preparation make it difficult or impossible for analyses to be carried out by untrained persons, since the sample preparation for meeting the stated requirements generally has to be performed by trained personnel. For example, there are at present no devices on the market, or only a small number of devices, with which the parameter HDLC can be measured. The main reason for this is that, because of the coagulation that occurs during the separation, this parameter can be measured only in plasma to which anticoagulants are added and using an exactly defined sample volume (for example 31±1.5 µl), that is to say only after very careful sample preparation.

A known method of obtaining plasma from blood samples, for example capillary plasma, is to obtain capillary blood and then carry out centrifugation. For example, blood emerging from an incision in a surface of the body can be collected by means of a capillary and then subjected to centrifugation.

Devices for collecting and centrifuging capillary blood are known in principle from the prior art. For example, U.S. Pat. No. 5,456,885 describes a tube for collecting, separating and dispensing a two-phase liquid. In the meantime, capillaries are also commercially obtainable which, after being filled, are broken at a predetermined break point in order to obtain an exact sample volume. Such capillaries are commercially available for example from Dr. Müller Gerätebau GmbH, D-01705 Freital, Germany, or are described, for example, in DE 295 20 918 U1. The broken capillary parts, with the amount of blood located therein, are then introduced into a sample vessel, for example a cup. Such sample vessels are then centrifuged in corresponding centrifuges. Alternatively, a sample of capillary plasma can also be obtained from capillary blood by directly collecting the capillary blood in the sample vessels. After the centrifugation, during which the corpuscular portion of the blood sample separates from the blood plasma, the desired quantity of excess plasma is pipetted off from the excess of blood plasma.

With this pipetting, however, there is generally the problem that this procedure has to be done extremely carefully, since there is a risk that, during the pipetting, the coagulum at the vessel base is touched and, as a result, non-plasma constituents are also pipetted. The plasma fraction can be contaminated in this way, as a consequence of which measurement values can be considerably influenced.

This risk of contamination of the plasma fraction can be reduced only by collecting unnecessarily large amounts of blood or of plasma. For example, about 5 to 7 times the amount of necessary plasma generally has to be collected as capillary blood, in order to be able to obtain the required amount of plasma without risk of contamination.

However, this removal of quite large amounts of blood causes considerable difficulties in itself. For example, amounts of approx. 31±1.5 µl of pure blood plasma are typically needed for conventional tests, for example for the quantitative detection of one or more of the abovementioned analytes. In the abovementioned methods, however, this assumes a high volume availability of a starting quantity of capillary blood, which is not always possible. For example, according to the above, approx. 150-200 µl of capillary blood would be needed for this purpose, which is often only achievable in practice with difficulty.

Capillaries with predetermined break points are also known from other prior art documents.

DE 101 06 362 A1 describes a device and a method for collecting aqueous liquid samples. A capillary and a closure element are used, which closure element, including the capillary segment surrounding it, can be broken off or broken open by means of a predetermined break point. Moreover, the capillary has, in its interior, a mixing element made of ferromagnetic material, and retaining elements which serve to retain the mixing element. However, these retaining elements, in combination with the ferromagnetic mixing element, have the effect that centrifugation of the capillary at high speeds can lead to damage to the capillary channel. As one possible design of a capillary end, a Luer cone among other things is described, i.e., a cone-shaped reduction of the external diameter in the area of the capillary end.

In practice, however, the devices and methods known from the prior art present many technical challenges and disadvantages. An important disadvantage lies in particular in the handling safety of the known devices. Thus, in particular, capillaries with predetermined break points have to be manually or automatically manipulated several times before a desired target constituent of the sample can be provided. This manipulation by its nature involves many shaking movements and repeated positioning of the capillary in a wide variety of positions and orientations, which can lead to distortion of the measurement result. This can lead to amounts of sample leaking out, to undesired mixing-together of constituents of the sample, or to metering artifacts.

SUMMARY OF THE INVENTION

It is against the above background that the present invention provides certain unobvious advantages and advancements over the prior art. In particular, the inventor has recognized a need for improvements in methods and devices for providing blood constituents.

Although the present invention is not limited to specific advantages or functionality, it is noted that the present invention provides a defined volume of a target constituent of a sample. In particular, the methods and devices described herein are intended to permit safe, constant and precise provision of a volume of a target constituent of a sample, in particular of a plasma constituent of a blood sample, while at the same time ensuring a high level of purity, without the risk of contamination of the target constituent by other constituents of the sample.

In accordance with one embodiment of the present invention, a metering capillary for providing at least one defined volume of a target constituent of a sample is provided comprising at least two openings positioned at opposite terminal ends of the metering capillary. At least one of the openings has at least one constriction positioned directly at the at least one opening. The constriction comprises at least one inwardly protruding circumferential edge of the metering capillary and is configured such that an internal diameter of the metering capillary is reduced in the area of the constriction to a value of 10% to 80% of the internal diameter in the area outside the constriction. The metering capillary also has positioned between the openings at least one partition line, which can optionally further comprise at least one predetermined break point and/or at least one partition marking.

In accordance with another embodiment of the present invention, a device for providing at least one defined volume of a target constituent of a sample is provided comprising at least one metering capillary as described herein and further comprising at least one separating device for carrying out a constituent separation for the at least partial separation of at least two constituents of the sample inside the metering capillary.

In accordance with yet another embodiment of the present invention, a method for providing at least one defined volume of a target constituent of a sample is provided comprising providing at least one metering capillary comprising at least two openings positioned at opposite terminal ends of the metering capillary. At least one of the openings, in particular a distal opening, has at least one constriction positioned directly at the at least one opening. The constriction comprises at least one inwardly protruding circumferential edge of the metering capillary and is configured such that an internal diameter of the metering capillary is reduced in the area of the constriction to a value of 10% to 80% of the internal diameter in the area outside the constriction. The metering capillary also has positioned between the openings at least one partition line. The method further comprises at least partly filling the metering capillary with the sample; carrying out a constituent separation for the at least partial separation of at least two constituents of the sample inside the metering capillary; and dividing the metering capillary into at least two partial pieces, wherein at least one of the partial pieces contains the defined volume of the target constituent.

These and other features and advantages of the present invention will be more fully understood from the following detailed description of the invention taken together with the accompanying claims. It is noted that the scope of the claims is defined by the recitations therein and not by the specific discussion of features and advantages set forth in the present description. The method described below can be carried out in particular using one or more of the described devices, and the devices can be designed to carry out a method according to the invention in one or more of the described variants. Accordingly, for possible embodiments of the method, reference can be made to the description of the devices, and vice versa.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

The invention is based on the recognition that the methods known from the prior art, in which capillary blood is first collected by means of a capillary, then the capillary is broken in order to generate a defined volume of blood, and this blood (if appropriate after an optional further treatment) is then centrifuged, can be greatly simplified and improved if the blood is not removed from the capillary before the centrifugation. The invention accordingly relates to methods and devices that can be used in particular for the collection and application of precisely defined volumes of blood plasma. A specially adapted metering capillary is used which, at least at one of its openings, has a constriction. Accordingly, the invention can involve a combination of collecting blood in a special capillary, collecting plasma by means of centrifugation of the blood inside this capillary, and, finally, carrying out volume-dosed plasma application by breaking off one end of this capillary with a precisely defined internal volume and emptying out this defined plasma volume for subsequent tests, for example by applying it to a test strip. The invention considerably minimizes the required amount of blood and makes the manual separating and pipetting step redundant. At the same time, the amount of plasma obtained is constant and precise in volume.

Generally, a method for providing at least one defined volume of a target constituent of a sample is provided. As explained above, this sample can be a blood sample in particular, for example capillary blood, and/or another sample of a body fluid. However, other samples can also be used in principle.

A target constituent can generally be understood as a constituent of the sample that it is of interest to provide, for example for making it available for a further use. As mentioned above, the target constituent can be blood plasma in particular. Providing is understood as collecting this target constituent and/or applying this target constituent, in particular applying it in at least one medical and/or diagnostic use. A "defined" volume is understood as a volume that can be provided in a reproducible manner within the scope of predetermined error limits, for example within the scope of error limits of not more than ±5%, typically not more than ±1%.

The method in accordance with embodiments of the present invention comprises the following method steps, which are typically, but not necessarily, carried out in the sequence described. Moreover, additional method steps not particularly described can be carried out. Moreover, individual method steps or several method steps can be repeated or carried out at the same time or overlapping in time.

In a first method step, at least one metering capillary is provided that has at least two openings. A metering capillary is understood as a capillary with a capillary channel whose dimensions are largely known. The dimensions should at least be known or reproducible to the extent that the above-described tolerances can be satisfied. The metering capillary and the metering channel can typically be substantially straight. However, other geometries are also possible in principle, for example a curved metering capillary, for example a metering capillary bent in a U shape.

The metering capillary has at least two openings. The openings can be arranged, for example, at the ends of the metering capillary or near the ends of the metering capillary, for example at a distance from the ends of not more than twenty times the external diameter of the metering capillary. Alternatively or in addition, at least one of the openings can also be arranged at another location of the metering capillary. For example, the metering capillary can have two openings opposite each other, for example at the opposite ends of the at least one capillary channel of the metering capillary. The metering capillary is therefore typically designed as a typically linear metering capillary open at both ends. As is explained in more detail below, these at least two openings can comprise at least a distal opening and at least a proximal opening. A proximal opening is understood as an opening through which filling takes place, whereas a distal opening is understood as another opening, through which no filling takes place.

According to the invention, at least one of the openings of the metering capillary has a constriction. A constriction in the context of the present invention is generally understood as a narrowing of the internal diameter of the metering capillary compared to the internal diameter of the metering capillary in the area surrounding the constriction, for example upstream and/or downstream of the constriction as seen in a longitudinal direction of the metering capillary. For example, the capillary channel outside the constriction can have a substantially constant internal diameter. However, other configurations are also possible in principle, for example conical capillary channels. The constriction can in particular narrow the internal diameter of the metering capillary to half or less, particularly to a quarter or less.

The constriction typically has a length, along a longitudinal extent of the capillary channel, that does not exceed twenty times the mean internal diameter of the capillary channel outside the constriction, and particularly typically does not exceed this by ten times or even five times or by twice. Accordingly, the constriction can be configured as a local narrowing of the internal diameter of the capillary channel. However, other configurations are also possible.

If one opening has such a constriction, this can mean, within the context of the present invention, that the constriction is arranged directly at the opening or in immediate proximity to the opening. Immediate proximity is to be understood, for example, as an arrangement at a distance from the opening that is not more than twenty times the opening diameter, typically not more than ten times the opening diameter, and particularly typically not more than five times the opening diameter, or even not more than twice the opening diameter. Since the opening, as stated above, can be arranged in particular at one end or near one end of the metering capillary, the constriction can therefore likewise be arranged in particular at the end or near the end. The constriction can therefore be configured in particular as an end-positioned constriction.

The constriction can, for example, comprise at least one inwardly protruding circumferential edge of the capillary. However, other constrictions in the form of other types of narrowing of the capillary are also possible. Generally, constrictions are technically simple to produce, for example by suitable extrusion methods for capillaries.

The constriction can be arranged in particular at one end of the metering capillary, which end is also designated herein below as the constriction end. The constriction can, for example, be designed in such a way that, by means of the constriction, an internal diameter of the metering capillary is reduced in the area of this constriction to a value of 10% to 80%, in particular to a value of 20% to 60%, and particularly typically to a value of approximately 40%, for example, 42% of the internal diameter in the area outside this constriction. In the area of the constriction, i.e., at the location of the metering capillary most narrowed by the constriction, for example at the constriction end, the internal diameter of the metering capillary is typically not more than 1.0 mm, particularly typically not more than 0.8 mm, in particular not more than 0.6 mm, for example 0.5±0.2 mm. For example, the internal diameter of the metering capillary in the area of the constriction can be between 0.2 mm and 0.8 mm, typically between 0.3 mm and 0.7 mm, and particularly typically 0.5 mm±0.2 mm. In the area outside the constriction, the metering capillary can, for example, have an internal diameter of 0.5 mm to 2.0 mm, particularly of 0.8 mm to 1.6 mm, typically of 1.0 mm to 1.4 mm, and particularly typically of 1.2 mm, for example 1.20±0.02 mm. The metering capillary can, for example, have a wall thickness of 0.05 mm to 3.0 mm, for example of 0.07 mm to 0.5 mm, and particularly typically of 0.1 to 0.2 mm, for example 0.175 mm±0.02 mm. In the undivided state, the metering capillary can, for example, have a length of 20 mm to 200 mm, typically of 30 mm to 120 mm, and particularly typically of between 70 mm and 80 mm, for example of 75.0 mm±0.5 mm. By means of the dividing procedure, the metering capillary can be divided into two parts for example, wherein the first partial piece, which typically faces the constriction end, has a length of, for example, between 5 mm and 60 mm, particularly of between 20 mm and 40 mm, and particularly typically of between 25 mm and 30 mm, for example of 28.0±0.9 mm. The volume received in the first partial piece can, for example, be a proportion of the total volume of the metering capillary of 10% to 70%, typically a proportion of 20% to 60%, and particularly typically a proportion of 30% to 40%, for example a proportion of 37%±2%.

This at least one constriction represents a considerable advantage of the metering capillary according to the invention over the devices known from the prior art. For example, DE 2 217 230 describes how, during the handling of the device proposed therein, a special hold is needed in order to avoid leakage of blood. Moreover, according to DE 2 217 230, the proposed device has to be manipulated very carefully, and it is essential for the capillary tube to be held in a horizontal position.

With the metering capillary of the embodiments of the present invention, and with the methods according to the embodiments of the present invention, these limitations in handling can be almost completely avoided. Thus, with the present invention, it is now no longer absolutely necessary to hold the metering capillary horizontal during the sampling procedure and the phase separation. Instead, with the constriction means, it is also possible without risking any leakage of the sample, to adopt inclined storage and handling positions and orientations, that is to say orientations in which a longitudinal direction of the metering capillary assumes an angle other than 0° to a horizontal plane, for example an angle of at least 20° or even at least 50°, and as far as an at least approximately vertical orientation. On the one hand, this increases the user-friendly nature of the method and of the metering capillary. On the other hand, however, it also greatly reduces the susceptibility to error, especially for medical uses, since errors induced by the user, for example by holding the metering capillary obliquely, now no longer necessarily lead to sampling artifacts and/or metering artifacts, for example caused by leakage of sample liquid and the resulting incomplete filling of the metering capillary, and, accordingly, to distorted measurement results.

At the same time, however, the metering capillary of the present invention, in contrast for example to the design described in the abovementioned DE 101 06 362 A1, is suitable for the method described in more detail below and involving the constituent separation inside the metering capillary and the subsequent division of the metering capillary into partial pieces. Thus, the metering capillary can in particular undergo centrifugation, without interference from a mixing element and retaining elements, and without risk of damage or mixing-together of the sample constituents. A breaking method can also be carried out in order to divide the constituents, for example at predetermined break points, without a mixing element and/or retaining elements being able to affect this process. Further particulars of these method steps are explained in more detail below.

In a further method step, the metering capillary is filled at least partly with the sample. The filling is carried out, for example, through one or more of the at least two openings, i.e., the proximal opening. The filling is typically at least substantially complete, such that the capillary channel is typically filled completely with the sample. For this purpose, a small amount of the sample can emerge from an opening not used for the filling, for example the abovementioned distal opening. Excess amounts emerging from the distal opening can be removed after the filling procedure, for example by being simply wiped off. However, incomplete filling of the metering capillary can in principle also take place, as long as the relevant parts of the capillary channel, the parts which later provide the defined volume, are filled substantially completely.

Furthermore, the method comprises carrying out a method step in which a constituent separation takes place for the at least partial separation of at least two constituents of the sample inside the metering capillary. In particular, in the case of a blood sample, these at least two constituents can comprise the already mentioned blood plasma and also corpuscular portions of the blood sample (coagulum). Alternatively, however, another type of separation is also possible, for example a separation into more than two constituents. In contrast to the methods known from the prior art, the constituent separation in this case takes place inside the capillary itself, without the sample being removed from the metering capillary. Thus, the method differs, for example, from the known methods in which a broken-off part of a capillary is placed in a centrifuge vessel in order to deliver its content there to the centrifuge vessel, and in order then to be subjected to centrifugation.

The constituent separation can in particular take place by the action of forces on the metering capillary and/or on the sample contained in the metering capillary. In particular, these can be weight forces and/or inertia forces. Weight forces can be used, for example, in the context of a static separation or sedimentation for the constituent separation. The inertia forces can, for example, comprise a centrifugal force which, for example by means of a centrifuge, in particular a hematocrit centrifuge or the like, are exerted on the metering capillary and/or the sample inside the metering capillary.

In a further method step, the metering capillary is divided into at least two partial pieces, wherein at least one of the partial pieces contains the defined volume of the target constituent.

This division of the metering capillary into the at least two partial pieces can be carried out in various ways, which are typically adapted to the constituent separation. For example, two partial pieces can be provided, such that, for example, the metering capillary can be divided into exactly two partial pieces that each correspond to the ends of the metering capillary. One of these partial pieces can then be used, for example, as target partial piece and can contain the defined volume of the target constituent. Alternatively, however, a division into several partial pieces is also possible, such that, for example, two ends of the metering capillary are broken off, and only a middle partial piece is used as target partial piece, which contains the defined volume of the target constituent. Various configurations are possible.

As explained above, the method can furthermore comprise providing the defined volume of the target constituent for at least a medical and/or diagnostic use. This provision can, for example, involve provision for an analysis method for the detection of at least one analyte in the target constituent and/or another method of determining at least one other property of the target constituent. For this provision, the defined volume of the target constituent can, for example, be dispensed from the target partial piece. In this case, for example, capillary forces can again be used, for example by means of a partial piece opening of at least one of the partial pieces, namely of the target partial piece with the defined volume of the target constituent received therein, being brought into contact with a test element and/or a sample carrier. This contact can be made, for example, by placing the partial piece opening onto the sample carrier. The test element and/or the sample carrier can, for example, be designed flat, for example as a test strip or a flat microscope slide. The partial piece opening from which the defined volume of the target constituent is dispensed, i.e., provided, can for example comprise an opening already present beforehand in the metering capillary, typically the distal opening or the proximal opening. Alternatively, however, the partial piece opening can also comprise at least one opening that is created only when the metering capillary is divided into the at least two partial pieces, for example an opening at a break edge. However, dispensing through an already existing opening is typical, since this opening remains defined at all times, even in different dividing procedures.

In the constituent separation, particularly in the case of a blood sample, corpuscular constituents of the blood sample can be at least partially separated from blood plasma under the action of centrifugal forces and/or gravitational forces. The metering capillary is then typically divided in such a way that the defined volume of the target constituent contains as far as possible only blood plasma. However, contamination by other blood constituents can be accepted if appropriate within predetermined tolerance limits Alternatively or in addition, other target constituents can of course also be selected. For example, corpuscular constituents can be specifically selected as target constituent. In the following, however, without limitation in respect of further possible embodiments, the selected target constituent is assumed to be blood plasma.

As explained above, the at least one target constituent is selected by virtue of the metering capillary being divided specifically in order to select the target constituent from the metering capillary after the constituent separation. This can be done in particular by dividing the metering capillary into at least two partial pieces. As is explained in detail below on the basis of an example, at least one mechanical breaking method can, for example, be used to divide the metering capillary. For example, the metering capillary can have at least one predetermined break point, for example in the form of a complete or partial circumferential notch. The term notch is to be interpreted broadly and comprises in principle any desired local reduction in wall thickness. For example, it can also include ground surfaces. In particular, the notch can be configured in such a way that, when broken, it leads to smooth breaks. It is also possible to provide several predetermined break points. The predetermined break point can, for example, have a notch with a notch depth of between 10 µm and 100 µm, in particular between 35 µm and 50 µm, at a wall thickness of between 150 µm and 300 µm, in particular between 175 µm and 200 µm. The ratio of the notch depth to the wall thickness can be between ¼ and ⅙, for example.

The metering capillary can furthermore comprise one or more visually discernible markings. The predetermined break point can in particular be marked by color, for example by one or more markings discernible to a user being provided on an outer face of the metering capillary in the area of the predetermined break point. For example, one or more ring marks can be provided on one or both sides of the predetermined break point, for example symmetrically with respect to the predetermined break point. This color marking can facilitate the handling of the metering capillary and in particular the division of the partial pieces.

The metering capillary can be divided, for example by suitable breaking, in such a way that, for example, the target volume comprises less than 50% of the capillary volume of the metering capillary, typically at most 45% and particularly typically 37%. For example, a capillary with a constant capillary diameter can be used. For example, the metering capillary can have a capillary volume of between 70 µl and 150 typically of between 80 µl and 90 µl, and particularly typically of 84 µl. Upon that division, the volume of the target constituent can be, for example, 31 µl, if the total capillary volume is approx. 84 µl.

Particularly when a capillary with a constant capillary diameter is used as metering capillary, the metering capillary can be divided, for example, into two or more partial pieces, for example by the breaking method described above. For example, the metering capillary can be divided in a ratio x. This ratio x then corresponds, for example, to the partial length of the capillary, in the partial piece containing the defined volume of the target constituent, in relation to the total length of the metering capillary and/or the total length of the originally filled metering capillary. This typical ratio derives from typical hematocrit values that occur in practice, which in most cases do not exceed 60%. In this way, for example by means of a ratio x of 37%, for example through suitable choice of the position of the predetermined break point, it is possible to ensure that, when using blood samples, the division always takes place within an area of the metering capillary filled exclusively with blood plasma. The defined volume of the target constituent can then be removed in particular from the smaller of the two partial pieces, that is to say the partial piece with the length of less than 50% of the total length of the metering capillary or typically of at most 45% and in particular of 37% of the total length of the metering capillary.

After the constituent separation has been carried out and before the metering capillary is divided, further steps can be performed, for example in order to determine further properties of the sample. For example, after the constituent separation has been carried out and before the metering capillary is divided, at least one intermediate analysis step can be performed. In this at least one intermediate analysis step, it is possible for example, from the at least partial separation of the at least two constituents of the sample, for example in the case of a blood sample of the blood plasma and of the corpuscular portions of the blood sample, inside the metering capillary, to draw conclusions concerning at least one property of the sample. For example, conclusions can be drawn concerning a proportion of corpuscular constituents of the blood sample, in particular concerning a hematocrit value.

This intermediate analysis step can be carried out in particular in a relatively simple way, for example by optical measurement and/or optical examination. This can be done fully automatically or also manually. For example, a metering capillary made of glass or of another at least partially transparent material can be used, such that the separation of the constituents inside the metering capillary can be monitored visually. In this way, by establishing the position of the at least one partition line between the at least two constituents, conclusions can be drawn, for example, concerning the at least one property, for example the hematocrit value. With a constant capillary diameter of the metering capillary, this can, for example, involve measuring the length of that part of the metering capillary filled with corpuscular constituents, for example using a simple ruler or other measuring scale, and comparing this length to the total length of the metering capillary or to the total filled length of the metering capillary, in order to calculate the hematocrit value.

As explained above, the at least one metering capillary provided can, for example, be designed as a linear metering capillary, but other designs are also possible. The metering capillary can, for example, have a distal end and a proximal end, wherein a distal opening is arranged at the distal end, and a proximal opening is arranged at the proximal end. The distal and proximal openings are therefore typically arranged at mutually opposite ends of the metering capillary.

According to the invention, at least one of the openings of the metering capillary has a constriction. Regarding the possible designs of the constriction, reference can be made to the description above. In particular, at least one distal opening can be designed with such a constriction. At least one proximal opening, that is to say an opening through which the metering capillary is filled, can be designed without such a narrowing. Alternatively or in addition to a constriction at the distal opening, other openings can of course also be provided with such constrictions, for example the proximal opening.

As explained above, the metering capillary can thus be filled in particular from the direction of the proximal opening. As also explained above, an amount of the sample can emerge at the distal opening during the filling procedure. This ensures that the metering capillary is filled completely. Before the constituent separation is carried out and/or at other times during the method, the emerging amount of the sample can be removed, for example by wiping the metering capillary or by other cleaning steps. If a metering capillary with a constriction in accordance with the present invention is used, this emergence of the sample at the distal end of the metering capillary can generally be prevented or at least reduced.

As explained above, after the metering capillary has been divided, and therefore after the defined volume of the target constituent has been obtained, this defined volume of the target constituent can be provided in particular for at least one medical and/or diagnostic use. This provision can be effected through at least one of the openings for example. For example, an opening facing the partition line can be used, for example an opening at a break point after the metering capillary has been broken. However, since the break edges may in some cases be undefined, it is particularly typical if the defined volume of the target constituent is provided for the at least one medical and/or diagnostic use through the opening that was originally present, for example the distal opening.

As explained above, the filling of the metering capillary is typically carried out in such a way that the metering capillary is filled substantially completely by the sample. This can be achieved, for example, by the emergence of a small amount of the sample from the distal opening. Before the constituent separation is carried out, in particular by a centrifugation method, at least one of the openings should be closed. The proximal opening in particular can be closed. Alternatively or in addition, however, another opening can also be closed, for example in each case the opening in the direction of which the sample is forced in the constituent separation. This can once again in particular be the proximal opening. However, other embodiments are also possible in principle.

The at least one opening can be closed in various ways. In particular, one or more of the following closure pieces can be used: a mastic; a cap, in particular a plastic cap, typically a silicone cap; a wax, in particular a hematocrit wax; a resin; an adhesive.

For the at least one metering capillary, it is possible in principle to use materials known from the prior art. For example, the at least one metering capillary can comprise at least one glass material and/or be made entirely of glass. However, other materials are also possible in principle, for example quartzes, ceramics, plastics or the like. In particular, the material used can be adapted to the specific dividing method employed. If breaking methods are used, then it is typical to use hard, brittle materials. If other dividing methods are used, for example cutting methods, then it is typical to use materials that can be easily cut, for example plastics. It is possible in particular to use transparent or at least partially transparent materials.

The metering capillary can in particular have a capillary internal diameter of between 0.5 mm and 4 mm, in particular of between 1.0 mm and 1.2 mm. These capillary diameters have proven suitable in practice for receiving a blood sample in particular. However, other capillary diameters are also possible in principle.

Moreover, the metering capillary can also comprise one or more active substances. In particular, the metering capillary can have at least one anticoagulant substance, that is to say an active substance that at least partially prevents coagulation of a blood sample. This active substance can, for example, be incorporated into the material of the metering capillary. However, it is particularly typical if, alternatively or in addition, the active substance is applied as a coating on the inner face of the metering capillary, particularly in the form of an anticoagulant coating. Customary anticoagulants can be used, for example an EDTA (ethylene diamine tetraacetate) coating and/or a heparin coating, for example Na-heparin and/or Li-heparin and/or ammonium heparin. However, other anticoagulants are also known and can be used alternatively or in addition.

In another typical embodiment of the metering capillaries, the metering capillary, at the opening provided with the constriction, that is to say at the constriction end, is smooth and/or plane. In particular, the metering capillary can be planar or flat at this constriction end. In particular, sharp break edges can be avoided in this way. The smooth and/or plane design can be produced, for example, by polishing and/or by heat treatment, for example thermal rounding. For example, the outer surface at the opening provided with the constriction can extend substantially perpendicular to a longitudinal axis of the metering capillaries, for example with a deviation of not more than 5° from 90° to a longitudinal axis of the metering capillaries. For example, "smooth" here can signify mean roughness values (rms roughness) of less than 100 μm, typically of less than 50 μm and particularly typically of even less than 20 μm or even less than 10 μm, less than 5 μm, or even less than 2 μm.

In this way, for example, the constriction end can be part of a first partial piece which is generated, for example, by a breaking method and which, after the constituent separation and the subsequent division of the metering capillaries into at least two partial pieces, contains the defined volume of the target constituent. As is explained in more detail below, the constriction end of the first partial piece can be brought into contact with at least one test element, for example with a test field and/or an application zone of the test element. Movements of the constriction end can also be made on the test element, for example circular movements, which help distribute the sample from the first partial piece on the test element. Damage to the test element is avoided by virtue of the typically smooth nature of the constriction end.

In addition to the described method in one of the described method variants, a metering capillary is also provided that may be suitable in particular for use in a method according to one of the preceding embodiments. This metering capillary comprises at least two openings. At least one of the openings has at least one constriction. The metering capillary also has, between the openings, at least one partition line, in particular at least one partition line with at least one predetermined break point. A partition line can generally be understood here as a line, in particular a line extending perpendicular to a longitudinal direction of the capillary, along which a division can be made, particularly in a way that is visible to a user. Alternatively or in addition to the predetermined break point, the partition line can also be configured in another way, for example with at least one partition marking, for example in the form of a ring marking or the like, which identifies a site of partition of the metering capillary when the metering capillary is divided into the at least two partial pieces. For further possible details, reference can be made for example to the present description.

In addition to the method and to the metering capillary in one or more of the embodiment variants described above, a device in accordance with yet another embodiment of the present invention is described herein for providing at least one defined volume of a target constituent of a sample, in particular of a blood sample, in particular for providing a defined volume of blood plasma. The device can in particular be designed to carry out a method according to one or more of the embodiment variants described above. The device comprises at least one metering capillary, in particular a metering capillary of the type described above. The metering capillary comprises at least two openings and at least one partition line, in particular a partition line with a predetermined break point and/or with at least one partition marking. The device furthermore comprises at least one separating device for carrying out a constituent separation for the at least partial separation of at least two constituents of the blood sample inside the metering capillary. This separating device can in particular comprise a centrifuge, for example a hematocrit centrifuge. For further optional embodiments of the device, reference can be made for example to the present description.

The device can furthermore comprise at least one holding device, which is designed to fix the metering capillary in a defined position for at least partial filling of the metering capillary with the sample. This defined position, which expression covers spatial positions and also orientations, can in particular be a substantially horizontal position. A substantially horizontal position is to be understood here as a position in which the metering capillary assumes an angle of 0° with respect to the horizontal, although slight deviations can also be tolerated, for example deviations by not more than 20°, typically by not more than 5°. However, other orientations are also possible in principle. For example, the holding device can comprise a capillary holder, for example in the form of a simple capillary clamp. Alternatively or in addition, the holding device can, for example, also be part of the separating device for carrying out the constituent separation, such that, for example, the above-described constituent separation can then also be carried out in the holding device.

The methods, metering capillaries and devices described herein in various embodiments have many advantages over known methods and devices of this kind. For example, the method in accordance with various embodiments permits the collection of an exactly defined sample of capillary plasma, for example exactly 31 μl from 84 μl of capillary blood, in a very simple way and independently of the actual hematocrit value. The metering capillary with the at least one constriction, typically at the distal end, proves advantageous in particular. The constriction can in particular, on the one hand, prevent leaking of the plasma during and after the division of the metering capillary, for example when the metering capillary is broken off, and also, on the other hand, can avoid the overfilling of the metering capillary during the filling operation, by discontinuing the capillary transport. A constriction of this type proves advantageous in principle, for example also for oblique storage of the metering capillaries.

The metering capillary can in principle be filled from the direction of one or more openings. The metering capillaries can be closed, for example, at the proximal end. Alternatively, a closure of the distal end is also possible in principle. The advantage in this case is that the closure, for example a mastic block, for closing the distal end of the metering capillary is contaminated less with the sample. Thus, the distal end can be closed with the mastic, which was not in contact on its outer face with the blood collection site, for example on a finger.

Figure 1:
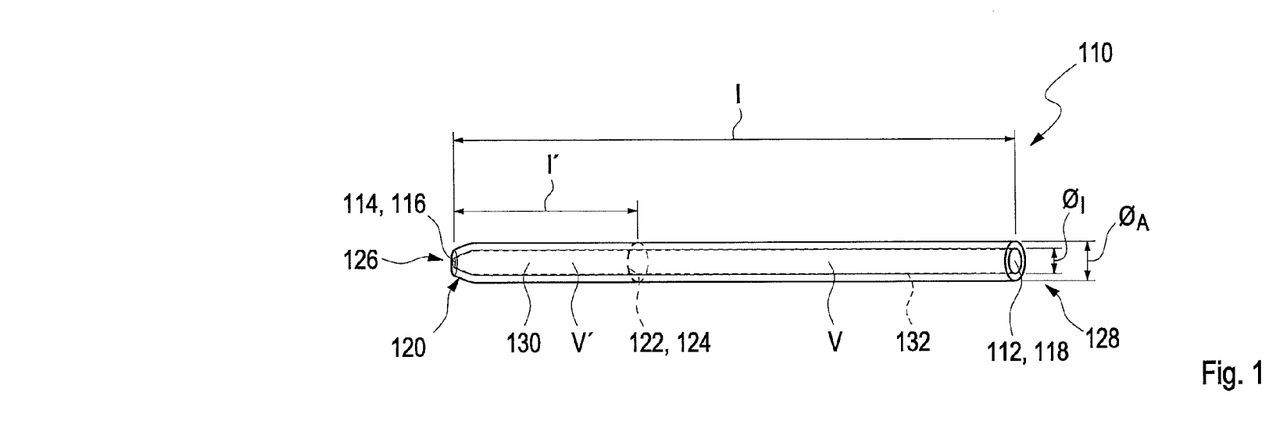
FIG. 1 shows an illustrative embodiment of a metering capillary according to the invention.

FIG. 1 shows a simple illustrative embodiment of a metering capillary 110 according to the invention. The metering capillary 110 is designed, for example, as a glass capillary and has, for example, a wall thickness of between 0.05 and 5 mm, in particular approx. 0.2 mm. The metering capillary has a length l of typically between 50 and 150 mm, in particular approx. 75 mm. The internal diameter of the metering capillary is, for example, between 1.1 and 1.2 mm, whereas the external diameter can be 1.6 mm, for example. The external diameter is designated in FIG. 1 by $\emptyset_A$, while the internal diameter is designated by $\emptyset_I$.

In the illustrative embodiment shown, the metering capillary typically has a substantially constant internal diameter $\emptyset_I$, such that the internal volume of the metering capillary 110 is distributed uniformly along the length of the metering capillary 110.

In the illustrative embodiment shown, the metering capillary 110 is designed as a straight metering capillary 110 open at both ends, with two opposite openings 112, 114. The first of these two openings 112, 114 is designated herein below as distal opening 116, while the second of these openings 112, 114 is designated as proximal opening 118. As can be seen from FIG. 1, the distal opening 116 has a constriction 120 in the illustrative embodiment shown. At this constriction 120, the internal diameter $\emptyset_I$ of the metering capillary 110 is, for example, reduced to a half, in particular to a quarter or less.

The metering capillary 110 also has a partition line 122. This partition line 122 can, for example, comprise a visually discernible marking. However, as is shown in FIG. 1, this partition line 122 particularly typically comprises a predetermined break point 124, at which the metering capillary 110 is notched. The notch depth of this notching can be, for example, 1/20 to 1/2, in particular 1/4 to 1/6, of the wall thickness of the metering capillary 110. For example, with a wall thickness of approx. 0.2 mm, a notch depth, for example a groove depth, of 35 μm to 50 μm is typical.

The partition line 122 is arranged at a distance l' from one of the two openings 112, 114, typically from the distal opening 116. The ratio of l' to l is also designated as x herein below. Typically, x is <50% and is in particular at most 45% or less, in particular 37%. Accordingly, a volume V' is received in the interior of the metering capillary 110 between the partition line 122 and a distal end 126 where the distal opening 116 is located, which volume V' (taking into account a possible slight deviation through the constriction 120 at the distal end 126) behaves like x with respect to the total volume V between the distal end 126 and a proximal end 128. For example, the total volume V can comprise approx. 84 μl while the defined volume V', which is also designated herein below by reference number 130, is typically 31 μl±1.5 μl. However, other volumes and divisions are possible in principle. In the method described below, the defined volume 130 receives the target constituent.

The metering capillary 110 can be optionally developed in various ways. For example, as is also indicated in FIG. 1, the metering capillary 110 can have, on its inner face, an anticoagulant coating 132, for example an EDTA coating.

FIGS. 2A to 2F show method steps of an illustrative embodiment of a method according to the invention for providing a defined volume of a target constituent of a sample 134. In the present example, the sample 134 is a blood sample, which is broken down into blood plasma and corpuscular constituents, for example In the text below, no distinction in terms is made between the sample 134 before and after the method, such that this sample is designated throughout by reference number 134. At the same time, these figures show the use of a metering capillary 110 and, in some parts, of a device 136 according to the invention for providing a defined volume of a target constituent of the sample 134.

Figure 2:
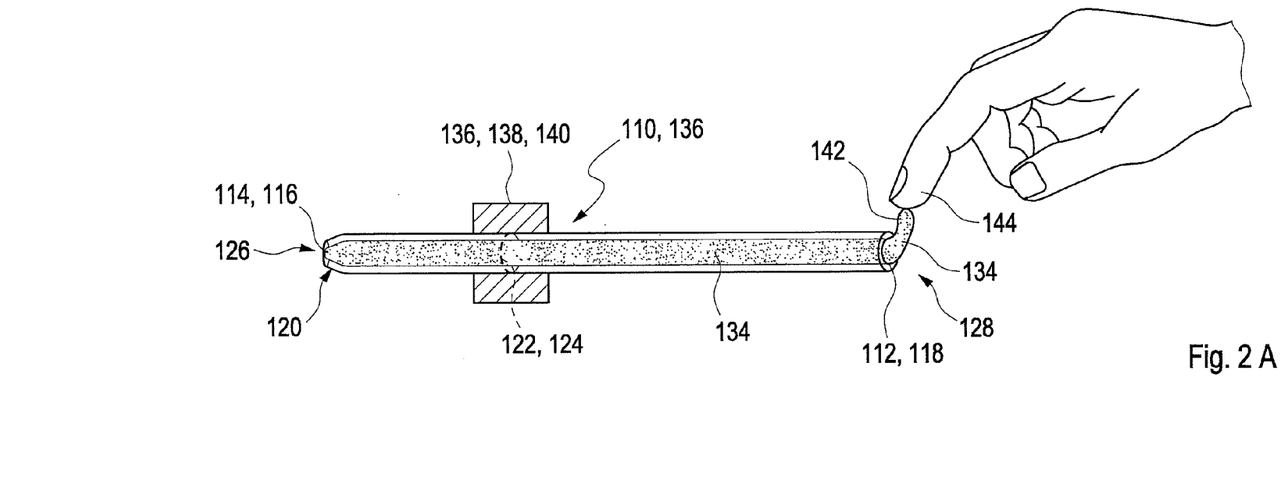
FIGS. 2A to 2F show method steps of an illustrative embodiment of a method according to the invention.

In FIG. 2A, a metering capillary 110 is first of all provided that is part of the device 136. For example, it can be a metering capillary 110 of the type described in FIG. 1. For example, it is possible to use an EDTA-coated metering capillary 110 with a capacity of approx. 84 μl, a length l of 75 mm and an internal diameter $\emptyset_I$ of 1.2 mm, which metering capillary 110 has a slight constriction 120 at its distal end 126. Moreover, the metering capillary 110 can have a partition line 122, in particular a predetermined break point 124, at a suitable location, for example at a distance l' of approx. 27 mm from the distal end 126.

FIG. 2A also shows a procedure in which the metering capillary 110 is filled with the sample 134, for example in the form of capillary blood, from the direction of one of its openings 112, 114. In the illustrative embodiment shown, this filling is done from the direction of the opening 112, which by definition therefore becomes the proximal opening 118.

Alternatively, however, filling could also take place from the direction of the other opening 114. The filling typically takes place at least more or less completely.

During the filling procedure, the metering capillary 110 can be received in a holding device 138, for example. This holding device 138 can be designed, for example, as a clamping device. As is indicated by reference number 140 in FIG. 2A, this holding device 138 can also be part of a separating device, for example of a centrifuge, in particular a hematocrit centrifuge. However, a separate holding device 138 is also conceivable in principle. The holding device 138 can be designed in particular to hold the metering capillary 110 in a horizontal position. In this way, the metering capillary 110 can be filled from a blood droplet 142 on a finger pad 144 of a patient. However, other types of samples can also be provided alternatively or in addition, for example samples from a separate container that is filled in advance with blood. However, filling directly from a blood droplet 142 has a great many advantages.

After the filling of the metering capillary 110 as shown in FIG. 2A, at least one opening 112, 114 of the metering capillary 110 is closed in a method step shown in FIG. 2B. The metering capillary 110 can still be received in the holding device 138, which is not shown in FIG. 2B. In the illustrative embodiment shown in FIG. 2B, the proximal opening 118 is closed. Generally, the opening 112, 114 that is closed can in particular be the one which, in a separation step described below and using a centrifuge as separating device 140, is located farthest away from the rotation axis of the centrifuge, such that the sample 134 is forced in the direction of the opening 112, 114 that is closed. In the present example, the closed opening is the proximal opening 118.

The opening 112, 114 can be closed, for example, with a closure piece 146, which can comprise, for example, a silicone cap, a hematocrit wax, a resin or a suitable adhesive.

During the filling of the metering capillary 110 as shown in FIG. 2A, but also during the closure of the proximal opening 118 with the closure piece 146, the constriction 120 at the opposite, distal end 126 of the metering capillary 110 has a positive effect in particular. Thus, this constriction 120 can prevent a relatively large amount of the sample 134 from running out of the distal opening 116 during the filling procedure or also when the closure piece 146 is being fitted. However, as is shown in FIG. 2B, a relatively small amount of the sample 134 can emerge from the distal opening 116 and can then be removed, for example by being simply wiped off. This excess, which emerges from the distal opening 116, is designated by reference number 148 in FIG. 2B.

FIG. 2C, finally, shows the filled metering capillary 110 closed with the closure piece 146. This metering capillary 110 can still be held in the holding device 138 which, once again, is not shown in FIG. 2C. However, another type of storage is also possible in principle, and alternatively or in addition a transport of the metering capillary 110. For this purpose, for example, the distal opening 116 can also be optionally closed, for example by a cap and/or by adhesive or by a similar closure.

Thereafter, a step shown symbolically in FIG. 2D and involving a constituent separation takes place (here shown in perspective from above). This constituent separation involves an at least substantial separation of a first constituent 150 of the sample 134, which first constituent 150 comprises corpuscular portions 152 of the sample 134, from a second constituent 154, which, in the example shown, comprises blood plasma 156. This is done, for example, using the above-described separating device 140, in particular a centrifuge.

The centrifuge can be designed, for example, as a hematocrit centrifuge or similar. In particular, a simple centrifuge can be used, without adjustment possibilities, for example with a predetermined speed of rotation and/or running time. The separation of the two constituents 150, 154 in this case takes place by centrifugal forces, wherein the denser, corpuscular portions 152 are driven toward the proximal end 128 of the metering capillary 110. By contrast, the lighter constituents of the blood plasma 156 settle toward the distal end 126. As is indicated in FIG. 2D, a phase limit 158 forms between the two constituents 150, 154. The position of this phase limit 158 is determined by the current hematocrit value. The position of the partition line 122, for example of the predetermined break point 124, is chosen in such a way that, at the usual hematocrit values, it is located within the area of the second constituent 154, but as close as possible to the phase limit 158. In particular, as described above, it can be arranged 30 mm away from the distal end 126.

In the separation step, air bubbles may possibly settle in the metering capillary 110 at the distal end 126. If this is the case, these air bubbles may, for example in a further and optional method step, be forced out to the distal opening 116, for example by means of mastic of the closure piece 146 being pushed in further at the proximal opening 118. For example, the proximal end 128 can be pressed back into a mastic composition after the separation step. It is thus possible to ensure that the defined volume 130 no longer contains any air bubbles.

After the separation step, the metering capillary 110 can be removed from the separating device 140, and divided into at least two partial pieces 160, 162. This is indicated in FIG. 2E by simple breaking of the metering capillary 110 along the predetermined break point 124. Alternatively, however, the metering capillary 110 can also be divided into more than two partial pieces.

By dividing the metering capillary 110 into the partial pieces 160, 162, a target constituent 164 is chosen. In this illustrative embodiment shown, this target constituent 164 is as large as possible a portion of the blood plasma 156, which forms the second constituent 154 of the sample 134. As has already been described with reference to FIG. 1, the target constituent 164 has the exactly defined volume V'.

Depending on the coating 132 of the metering capillary 110 for example, the blood plasma 156 obtained in this way in the target constituent 164 can have various anticoagulants added to it. However, it is also possible for blood plasma 156 to be prepared from non-anticoagulated blood, for example by the procedure being carried out suitably quickly.

Figure 2F:
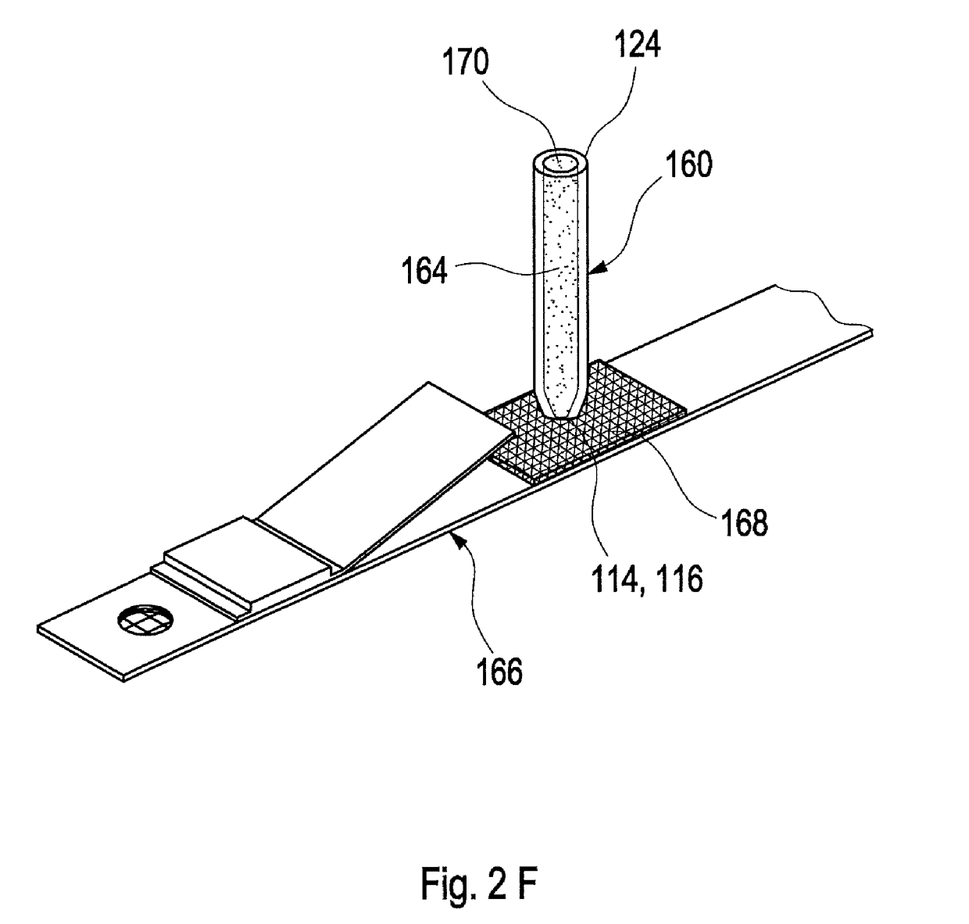

As described above, the target volume of the target constituent 164 that is centrifuged off can be, for example, precisely 31 μl. This target constituent 164 can be applied, for example, to a test element 166. An example of this is shown in FIG. 2F. Here, a test element 166 is shown by way of example in the form of a test strip, which has at least one test field 168. For example, this test field 168 can comprise a suitable test chemical. For example, an HDLC reagent holder for an analyzer of the Reflotron® type (Roche Diagnostics) can be used. The target constituent 164 in the first partial piece 160 can be applied, for example, by bringing the distal opening 116 with the constriction 120 into contact with a carrier mesh of the test field 168. Alternatively, however, an opening 170 facing the predetermined break point 124, and arising from the division of the two partial pieces 160, 162 shown in FIG. 2E, can be applied to the carrier mesh. However, preference is given to the variant shown, in which one of the original openings 112, 114, typically an opening 114 with a constriction 120, is applied to the test field 168, since this opening provides a more defined interface, for example a smooth, smoothed or polished interface. After the application to the test element 166, it is possible, for example, to carry out a measurement of a property of the sample 134, which is now a plasma sample, for example a qualitative and/or quantitative detection of at least one analyte in the plasma sample. For example, HDLC can be detected.

Furthermore, the described method and the illustrated device 136 also permit the determination of other properties of the capillary blood sample. Thus, one or more intermediate analyses can also be performed, for example after the separation step shown in FIG. 2D, but before the step shown in FIG. 2E involving the division of the two partial pieces 162, 164. For example, the position of the phase limit 158 can be determined, for example by means of a suitable measuring device. In this way, for example, a conclusion can be directly drawn concerning the proportion of the corpuscular portions 152 and thus concerning the hematocrit value of the sample 134. This can be done, for example, by using a calibrated rule to determine the length of the erythrocyte column, i.e., the length of the corpuscular portions 152 of the first constituent 150. Since the metering capillary 110 is filled uniformly and typically completely, a nomogram, similar to that for the hematocrit determination from hematocrit tubes, is generally not necessary.

After the measurement, both partial pieces 160, 162 of the metering capillary 110 can be discarded or used for further measurements. The techniques required to produce the metering capillary 110 with suitable markings and/or predetermined break points 124 are known in principle to a person skilled in the art. The required precision in terms of the amount of target constituent 164 to be obtained, for example of blood plasma, is not a problem from the point of view of production engineering.

There are also generally no demands concerning the precision of the speed of rotation and/or running time of the separating device 140, for example of the centrifuge. The centrifugal forces that arise should be selected to be as low as possible, in order not to place too great a load on the seal at the closure piece 146 at the proximal end 128 of the metering capillary 110. For example, it is possible to use relative centrifugal forces (rcf) of 5,000 g to 10,000 g, in particular of 7,000 to 9,000 g, and particularly typically 8,000 g, where g is the gravitational acceleration. The capillary dimensions described are, for example, for a hematocrit value of up to 60%, which is sufficient for obtaining 31 μl of blood plasma.

By suitable positioning of the predetermined break point 124 at the distal end 126 of the metering capillary 110 or by changes in the internal diameter of the metering capillaries 110, it is also possible to obtain other defined quantities of plasma or other quantities of target constituent 164. This does not change the basic procedure.

It is noted that the described metering capillary 110 can also be used without a separation step being carried out. For example, a predetermined amount of blood can be applied by means of the metering capillary 110 without a centrifugation step.

It is also noted that the method is shown only symbolically in FIGS. 2A-2F and can be modified in any desired way within the scope of the present invention. For example, the constriction 120 can also be provided alternatively or in addition at another opening 112, 114. Moreover, the filling can also take place from the direction of another opening 112, 114. A number of variations of the disclosed method are conceivable.

As described above, the constriction 120 has, among other things, the effect of considerably improving and facilitating the handling of the metering capillaries 110. In particular, it provides increased handling safety by virtue of protecting against undesired leakage. Various tests were carried out to confirm this.

In order that the invention may be more readily understood, reference is made to the following example(s), which are intended to illustrate the invention, but not limit the scope thereof.

In these tests, a metering capillary 110 was used in conjunction with samples in the form of fresh capillary blood (also designated herein below by "C") or venous blood (also designated herein below by "V"). The metering capillary 110 was coated with EDTA and had a constriction 120. The metering capillary 110 had a length of 75.00 mm±0.50 mm, an internal diameter of 1.20 mm±0.2 mm, an external diameter of 1.55 mm±0.02 mm, and a length of the first partial piece 160 of 28.00 mm±0.90 mm In the area of the constriction 120, the metering capillary 110 had an internal diameter of 0.50 mm±0.20 mm The predetermined break point 124 was marked on both sides by black ring marks with a width of 0.80 mm±0.10 mm, which marks were each arranged at a distance of 1.0 mm±0.20 mm from the predetermined break point 124.

The metering capillary 110 was filled completely with the sample 134 and held tilted, in each case for 5 seconds, at a predetermined tilt angle with respect to a horizontal. Separate measurements were carried out for both tilting directions, that is to say once in each case for a tilt at which the opening 114 provided with the constriction 120 pointed downward (also designated herein below by "constriction end down" or "CD") and once in each case for a tilt at which the opening 112 without constriction 120 pointed downward (also designated herein below by "open end down" or "OD").

The results of these measurements are shown in Table 1. The abbreviations "C", "V", "CD" and "OD" used in this Table 1 have already been explained above. Moreover, in the columns designated by the tilt angles, Table 1 also shows, for each test, whether the sample 134 used in the test was retained in the metering capillary 110 (designated by "+") or leaked out (designated by "−").

The results in Table 1 show that, with one exception (number 6), both types of blood (capillary and venous) meet the test conditions up to an angle of 30°. This ensures sufficient safety against leakage during the handling of the metering capillaries 110, for example during removal from a holder, during closure with hematocrit wax, or during similar handling procedures. Completely filled metering capillaries 110 with these dimensions but without the constriction 120 leak even when held at a tilt angle of approx. 5°, as can also happen unintentionally during handling. In addition, the constriction 120 allows the metering capillary 110 to be turned quickly in one movement through 180°, which is likewise not possible without the constriction 120. Thus, the constriction 120 provides an added safety feature during the handling of the metering capillary 110.

TABLE 1

Test results for leakage of sample from metering capillaries with constriction at different tilt angles

| No. | Sample | Tilt direction | 5° | 10° | 15° | 20° | 25° | 30° | 35° | 40° |
|---|---|---|---|---|---|---|---|---|---|---|
| 1 | C | CD | + | + | + | + | + | + | − | − |
| 2 | C | OD | + | + | + | + | + | + | − | − |
| 3 | C | CD | + | + | + | + | + | + | + | − |
| 4 | C | OD | + | + | + | + | + | + | − | − |
| 5 | C | CD | + | + | + | + | + | + | + | − |

TABLE 1-continued

Test results for leakage of sample from metering capillaries with constriction at different tilt angles

| No. | Sample | Tilt direction | 5° | 10° | 15° | 20° | 25° | 30° | 35° | 40° |
|---|---|---|---|---|---|---|---|---|---|---|
| 6 | C | OD | + | + | + | + | + | − | − | − |
| 7 | V | CD | + | + | + | + | + | + | + | − |
| 8 | V | OD | + | + | + | + | + | + | − | − |
| 9 | V | CD | + | + | + | + | + | + | + | − |
| 10 | V | OD | + | + | + | + | + | + | − | − |
| 11 | V | CD | + | + | + | + | + | + | + | − |
| 12 | V | OD | + | + | + | + | + | + | − | − |
| 13 | C | CD | + | + | + | + | + | + | − | − |
| 14 | C | OD | + | + | + | + | + | + | − | − |
| 15 | C | CD | + | + | + | + | + | + | − | − |
| 16 | C | OD | + | + | + | + | + | + | − | − |
| 17 | V | CD | + | + | + | + | + | + | + | − |
| 18 | V | OD | + | + | + | + | + | + | − | − |
| 19 | V | CD | + | + | + | + | + | + | + | − |
| 20 | V | OD | + | + | + | + | + | + | − | − |

The holding time of 5 seconds used in the described tests offers sufficient time in practice for handling of the metering capillaries 110 by hand. The tests also showed that none of the users handling the metering capillaries 110 had the mishap of having the metering capillary 110 leak during the tests. However, with open hematocrit capillaries that are completely filled, such mishaps occur frequently in practice. Moreover, the tests revealed that, after optional closure at one end, for example with hematocrit wax, the metering capillary 110 with the constriction 120 was protected even completely against leakage, at least until the dividing procedure was carried out.

The constriction 120 is typically only provided at one end, as also in the described tests. Another reason for arranging the constriction 120 at one end is the leakage behavior of a broken-off part of the metering capillaries 110, for example of the first partial piece 160 in FIG. 2E. The content of this first partial piece 160, for example its content of plasma, should be applied completely, for example after centrifugation, to the test element 166, for example a Reflotron® HDLC test support. However, in many cases this only functions if the first partial piece 160 is placed without pressure on the test field 168 and/or an application zone, for example the yellow application field in the Reflotron® HDLC test support, and moved in a gently circulating movement until completely emptied. The constriction end with the constriction 120 is in many cases ground smooth or rounded, for example thermally rounded. By contrast, if the other end of the first partial piece 160 were to be used for the movement during application, the test field 168 could be easily damaged and rendered unusable by the rubbing of the sharp-edged capillary end of this first partial piece 160, for example on a cover fabric of this test field 168. Therefore, the constriction end is particularly typically planar.

The metering capillary 110 is also typically filled with sample 134 via the constriction end. Accordingly, after the filling procedure, the metering capillary 110 is generally contaminated on the outside with sample 134, for example with blood, exclusively at the constriction end. However, cleaning the metering capillary 110 from the outside is comparatively difficult in practice and requires skill. For example, wiping the metering capillaries 110 with open capillaries requires skill and speed, for example in order to ensure that a cellulose cloth used for wiping does not also withdraw some of the sample 134, for example the blood, from the metering capillary 110, for example through the force of its suction. By contrast, if a constriction 120 is used, the cleaning procedure is in practice completely uncritical because of this constriction 120 and can also be easily carried out by an untrained person. The increased capillary force in the constriction 120 reliably prevents sample 134, for example blood, being withdrawn by the wiping cloth.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A metering capillary for providing at least one defined volume of a target constituent of a sample, said metering capillary having at least two openings, wherein
   the openings are positioned at opposite terminal ends of the metering capillary;
   at least one of the openings has at least one constriction, wherein said constriction
      is positioned directly at said at least one opening,
      is formed by at least one inwardly extending circumferential edge of said metering capillary, and
      is configured such that an internal diameter of the metering capillary is reduced in the area of the constriction to a value of 10% to 80% of the internal diameter in the area outside the constriction; and
   the metering capillary also has positioned between the openings at least one partition line with at least one predetermined break point.

2. The metering capillary of claim 1, wherein the metering capillary has a capillary volume, and wherein the defined volume of the target constituent comprises less than 50% of the capillary volume.

3. The metering capillary of claim 1 further comprising at least one anticoagulant substance incorporated into a material forming the metering capillary or applied as a coating on an inner face of the metering capillary.

4. The metering capillary of claim 3, wherein the anticoagulant substance is an anticoagulant coating.

5. The metering capillary of claim 4, wherein the anticoagulant coating is ethylene diamine tetraacetate (EDTA).

6. The metering capillary of claim 1, wherein a face of the metering capillary defining the at least one opening having the at least one constriction is smooth and/or plane.

7. The metering capillary of claim 6, wherein the face of the metering capillary defining the at least one opening having the at least one constriction is polished and/or rounded by heat treatment.

8. A device for providing at least one defined volume of a target constituent of a sample, comprising
at least one metering capillary of claim 1, and
at least one separating device for carrying out a constituent separation for the at least partial separation of at least two constituents of the sample inside the metering capillary, wherein said separating device further comprises a holding device configured to fix the metering capillary.

9. The method of claim 8, wherein the separating device is a centrifuge or comprises as centrifuge.

10. The device of claim 8, wherein the holding device is configured to fix the metering capillary in a defined position for at least partial filling of the metering capillary with the sample.

11. The device of claim 8, wherein the holding device is configured to fix the metering capillary in a substantially horizontal position.

12. A method for providing at least one defined volume of a target constituent of a sample comprising:
providing at least one metering capillary having at least two openings, wherein
the openings are positioned at opposite terminal ends of the metering capillary,
at least one of the openings has at least one constriction, wherein said constriction
is positioned directly at said at least one opening,
is formed by at least one inwardly extending circumferential edge of said metering capillary, and
is configured such that an internal diameter of the metering capillary is reduced in the area of the constriction to a value of 10% to 80% of the internal diameter in the area outside the constriction, and
the metering capillary also has positioned between the openings at least one partition line with at least one predetermined break point;
at least partly filling the metering capillary with the sample;
carrying out a constituent separation for the at least partial separation of at least two constituents of the sample inside the metering capillary; and
dividing the metering capillary into at least two partial pieces, wherein at least one of the partial pieces contains the defined volume of the target constituent.

13. The method of claim 12 further comprising applying the defined volume of the target constituent from a partial piece opening of at least one of the partial pieces to a test element and/or a sample slide.

14. The method of claim 12, wherein the sample comprises a blood sample, wherein the constituent separation involves corpuscular constituents of the sample being separated at least partially from blood plasma by the action of centrifugal forces and/or gravitational forces, and wherein the metering capillary is divided in such a way that the defined volume of the target constituent contains exclusively blood plasma.

15. The method of claim 12, wherein the metering capillary has a capillary volume, and wherein the defined volume of the target constituent comprises less than 50% of the capillary volume.

16. The method of claim 12 further comprising at least one intermediate analysis step carried out after the constituent separation has been carried out and before the metering capillary is divided, wherein the at least partial separation of the at least two constituents of the sample inside the metering capillary allows conclusions to be drawn concerning at least one property of the sample.

17. The method of claim 16, wherein the at least one property of the sample is a proportion of corpuscular constituents in the sample.

18. The method of claim 12 further comprising closing at least one of the openings with an element before the constituent separation is carried out, said element selected from the group consisting of a mastic, a cap, a wax, a resin, and an adhesive.

19. The method of claim 18, wherein the cap is a plastic cap or a silicone cap, and wherein the wax is a hematocrit wax.

20. The method of claim 18, wherein the at least one opening is a proximal opening.

* * * * *